(12) United States Patent
Jadhav et al.

(10) Patent No.: US 6,875,381 B2
(45) Date of Patent: Apr. 5, 2005

(54) PROCESS FOR PREPARATION OF CHEMICALLY STABLE, DRY-FLOW, LOW COMPACT, DUST FREE, SOLUBLE GRANULES OF PHOSPHOROAMIDOTHIOATES

(75) Inventors: Prakash Mahadeo Jadhav, Mumbai (IN); Rajju Devidas Shroff, Mumbai (IN)

(73) Assignee: United Phosphorus, Ltd., Mumbai (IN)

( * ) Notice: Subject to any disclaimer, the term of this patent is extended or adjusted under 35 U.S.C. 154(b) by 367 days.

(21) Appl. No.: 10/126,965

(22) Filed: Apr. 22, 2002

(65) Prior Publication Data

US 2003/0127761 A1 Jul. 10, 2003

Related U.S. Application Data

(60) Provisional application No. 60/340,272, filed on Dec. 18, 2001.

(51) Int. Cl.[7] ............................... B29B 9/00
(52) U.S. Cl. .................... 264/37.29; 264/140
(58) Field of Search .................. 514/120, 137, 514/75; 424/710; 264/37.29, 140, 330

(56) References Cited

U.S. PATENT DOCUMENTS

| | | |
|---|---|---|
| 3,716,600 A | 2/1973 | Magee |
| 3,845,172 A | 10/1974 | Magee |
| 3,914,417 A | 10/1975 | Magee |
| 4,218,444 A | 8/1980 | Koundakjian |
| 4,544,553 A | 10/1985 | Smolanoff |
| 5,075,058 A | 12/1991 | Chan |
| 5,100,667 A | 3/1992 | Chan |
| 5,298,501 A | 3/1994 | Cummings |
| 5,352,674 A | 10/1994 | Cummings |
| 5,369,100 A | 11/1994 | Cummings |
| 5,443,764 A | 8/1995 | Lloyd |
| 5,464,623 A | 11/1995 | Chan |
| 5,488,043 A | 1/1996 | Yamada |
| 5,622,658 A | 4/1997 | Lloyd |
| 5,650,163 A | 7/1997 | Cannelongo |
| 5,698,540 A | 12/1997 | Katayama |
| 6,013,272 A | 1/2000 | Cummings |
| 6,337,323 B2 | 1/2002 | Cummings |
| 6,387,388 B1 | 5/2002 | Misselbrook |
| 2001/0018063 A1 | 8/2001 | Cummings |
| 2002/0091106 A1 | 7/2002 | Cummings |
| 2002/0114821 A1 | 8/2002 | Lescota |

FOREIGN PATENT DOCUMENTS

| | | |
|---|---|---|
| EP | 0304492 B1 | 12/1994 |
| JP | 58067603 | 4/1983 |
| JP | 6-92803 | 4/1994 |
| JP | 9-124406 | 5/1997 |
| WO | WO 98/26656 | 6/1998 |

OTHER PUBLICATIONS

International Specialty Products, "Granules & Tablets," Agrimer Polymers & Copolymers, International Specialty Products.
Fuji Paudal Co., Ltd., "Powder & Granulation Process Technology," Fuji Paudal Co., Ltd.

Primary Examiner—Mark Eashoo
(74) Attorney, Agent, or Firm—Jones, Tullar & Cooper, PC

(57) ABSTRACT

Dry flow, low compact, dust free, soluble granules of phosphoroamidothiates, preferably acephate, are produced by the process of 1) pre-mixing technical grade phosphoroamidothioate with specified adjuvants and other inert ingredients; 2) grinding to produce a ground product having a preferred particle size of 5 microns to 10 microns; 3) post-mixing; 4) granulating; 5) drying; 6) sizing to required length, preferably 1.5 to 3.0 mm; 7) and sieving to remove the fines to get the desired dust free soluble granule.

68 Claims, 1 Drawing Sheet

PROCESS FOR PREPARATION OF CHEMICALLY STABLE, DRY-FLOW, LOW COMPACT, DUST FREE, SOLUBLE GRANULES OF PHOSPHOROAMIDOTHIOATES

CROSS REFERENCE TO RELATED APPLICATION

This application claims the benefit, under 35 U.S.C. 119(e), of U.S. Provisional Application No. 60/340,272 filed Dec. 18, 2001, the contents of which are incorporated herein by reference.

BACKGROUND OF THE INVENTION

1. Field of the Invention

The present invention relates to a process for preparing insecticidally active soluble granules of phosphoroamidothioate, referred to herein as acephate.

2. Background Information

In recent years, agricultural chemicals have been most preferably formulated in the form of dusts, wettable powders, soluble powders, emulsifiable concentrates, soluble liquid/concentrates, granules, coated granules, water dispersible granules, suspension concentrates, and solutions. Occasionally, when dusts are produced by absorbing or mixing active ingredients with a finely divided inert carrier material, for example China Clay or the like, drift problems occur. With wettable powders and soluble powders the problems faced at the time of dilution are not only drift, but the final disposal of containers, for dust particles tend to stick to sides of the containers. The left over materials within the containers pose great problems to the environment, operators and users.

Although dusts are undesirable because of airborne contamination and handling difficulties, liquid spray formulations have not provided an acceptable alternative, for they involve solvents and packaging expenses, along with container disposal requirements that detract from their commercial desirability.

Water dispersible granules produced by fluidized bed spray dryers overcome the problems associated with wettable powders and soluble powders, but have high processing costs and require high value capital investment, as well as requiring highly skilled staff. These problems impose a significant barrier in widening the market acceptance of these compounds.

Certain phosphoroamidothioates and phosphoroamidodithioates, collectively referred to as Phosphoroamidothioates, are known to have excellent insecticidal activity against a variety of insects and in a variety of environments. Acephate, one of the important commercial insecticides within this class of compounds, is a systemic and contact insecticide of moderate persistence with residual activity lasting about 10–15 days. It is effective against a wide range of aphids, leaf-miners, lepidopterous, larvae, sawflies and thrips and it is also a non-phytotoxic on many crop plants.

Phosphoroamidothioate containing pellets have been proposed in the past, but difficulties have been encountered in pelletizing acephate technical, the preferred insecticide within the class of phosphoroamidothioates. Attempts to manufacture acephate technical pellets from acephate technical powders have been proposed and have been unsuccessful.

Considerable experimentation in the area of producing the preferred high-strength acephate granules has been conducted and confirms the manufacturing difficulties which earlier formulators have experienced. Furthermore, the pellets and methods proposed for making pellets suggested in the prior art leave considerable room for improvement. Prior extrusion processes have proposed the addition of costly surfactants, the combination of phosphoroamidothioate with a second active ingredient, or the creation of a mixture of the active ingredient with a solvent in an amount of from 3–25% by weight before extrusion, but these processes have not solved the problems encountered.

The formulation of acephate presently in use is acephate 75% soluble powder having acephate active ingredient 75% (w/w), surfactant 1 to 2% (w/w), inert filler (precipitated silica) to make 100% (w/w). Acephate 75% soluble powder poses the problems of dust, low pourability, high transportation costs, high capital manufacturing investment, measurement difficulties, difficulties in packing material disposal, handling problems, high risk of caking and others.

Because of the problems associated with producing granular forms of phosphoroamidothioates, such as the preferred acephate, there is a need in the art for a process for preparing chemically stable, dry flow, low compact, dust free, insecticidally active soluble granules of phosphoroamidothioate which are useful from a practical stand point, as well as for a low cost, practical manufacturing technique which can be practiced on a commercial scale without requiring expensive additives or solvents.

SUMMARY OF THE INVENTION.

By the present invention the above-identified major limitations have been overcome. The method for producing dry flow, low-compact, dust free, soluble phosphoroamidothioate granules, such as the preferred compound acephate, is an improvement over prior manufacturing processes. Further, the dust free soluble granules produced by this invention, which has a concentration of the insecticidally active ingredient in this formulation may vary from 40–98% of phosphoroamidothioate active ingredient, is more advantageous than prior granular products and exhibits certain very desirable characteristics as noted hereinafter.

Briefly, and in accordance with a preferred embodiment of the invention, dry flow, low compact, dust free, soluble granules of insecticially active phosphoroamidothioate are prepared by forming a pre-mix containing the required quantity of phosphoroamidothioate, a dispersing agent, a wetting agent, a binding agent, an antifoaming agent, a disintegrating agent, a stabilizer and filler. The specified adjuvants have a maximum of 1% water insoluble matter. This pre-mix is then ground to produce a ground product having preferred particle sizes between 5.0 microns to 10.0 microns. The ground product is fed to a post-mixer to form a mixture. The mixture is then fed through a hopper into a granulator where granules are formed. The granules are then dried, and the dried granules are sized and sieved to separate dry granules from fines, producing dry flow, low compact, dust free, soluble granules of phosphoro-amidothioate as noted above, the preferred phosphoroamidothioate is acephate. The fines may be recycled back to the post mixer.

This invention produces essentially dry flow, low compact, dust free soluble phosphoroamidothioate granules having a preferred granule size of 1.5 to 3.0 mm in length and 0.5 to 1.0 mm in diameter. These granules of phosphoroamidothioates are characterized by aging stability for a minimum of two years.

BRIEF DESCRIPTION OF THE DRAWINGS

The features and advantages of the present invention will become apparent from the following detailed description of preferred embodiments thereof, taken in conjunction with the accompanying drawings, in which.

DETAILED DESCRIPTION OF THE PREFERRED EMBODIMENTS

Figure 1:
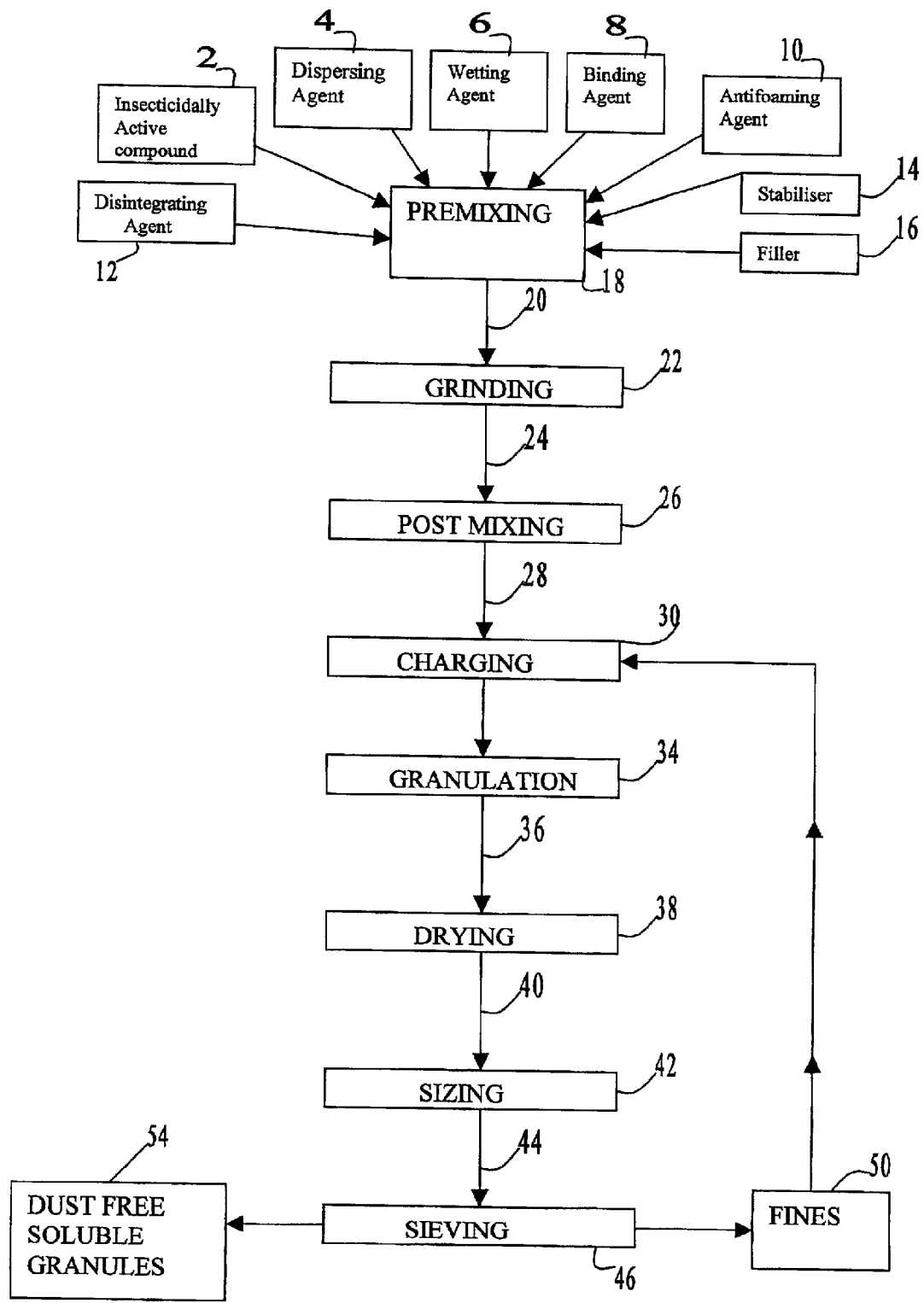
FIG. 1 is a flow chart of the preferred embodiment of the present invention.

The process of the present invention is best described by referring to the flow chart in FIG. 1. An essentially dry pre-mix comprising about 95% to 99% of solids and 1% to 5% moisture and/or solvent is formed from the following ingredients: 40% to 98% of the insecticidally active compound 2, 0.1% to 5.0% dispersing agent 4, 0.1% to 3.0% wetting agent 6, 0.1% to 3.0% binding agent 8, 0.01% to 0.08% antifoaming agent 10, 0.01% to 10.0% disintegrating agent 12, 0.01% to 1.0% stabilizer 14, and fillers 16 to make 100% (w/w). The insecticidally active compounds of the present invention have the following formula:

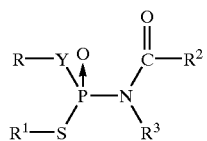

wherein R and $R^1$ individually are an alkyl, alkenyl or alkynyl group containing upto 6 carbon atoms, $R^2$ is hydrogen, an alkyl group containing 1 to 18 carbon atoms, a cycloalkyl group containing 3 to 8 carbon atoms, an alkenyl group containins 2 to 18 carbon atoms or an alkynyl group containing 3 to 18 carbon atoms, $R^3$ is hydrogen or an alkyl group containing 1 to 6 carbon atoms, and Y is oxygen or sulfur. All of the inert ingredients are preferably solids and in a powder form. In one preferred embodiment, the binding agent 8 is selected from sucrose and starch derivatives or a blend thereof, the wetting agent 6 is selected from calcium or sodium salt of alkyl aryl sulphonate, the dispersing agent 4 is selected from the derivative of sulfonated fatty alcohols, the disintegrating agent 12 is selected from swelling type clays such as Bentonite and zeolite, the antifoaming agent 10 is selected from silicon oil derivatives, the stabiliser 14 is selected from salts of higher fatty acids, and the filler 16 is selected from precipitated silica and kaoline and the like. Grinding 22 of the pre-mix 20 is then conducted, preferably in a microniser, to obtain a ground product 24 having a preferred particle size of 5 microns to 10 microns.

The ground product 24 is subjected to post-mixing 26 to form a mixture 28 which is then made into granules 36 by preferably charging 30, by way of a rotary feeder, a feeding hopper which supplies the mixture to a granulator for granulation 34. The granulator that performs the granulation 34 has a preferred inlet temperature between 30 to 35° C. and a preferred outlet temperature of between 40° C. to 45° C. The resulting granules 36 are subjected to a drying 38 process, preferably by passing the granules 36 through an air chamber, producing dry granules 40.

Sizing 42 the dry granules 40 is then accomplished to produce sized granules 44 of a desired length and diameter. Sizing the granules is preferably conducted by passing the dry granules 40 through an oscillating cutter to obtain granules which are preferably between about 1.5 mm and 3.0 mm in length and 0.5 mm to 1.0 mm in diameter. After sizing, the sized granules 44 are subjected to sieving 46 to separate fines 50 generated during the sizing process from desired dust free soluble granules 51.

The fines 50 from the sieving 46 process may be collected and recycled at the charging 30 stage of the process to obtain a minimum yield of 99.0% dry flowable, low compact, dust free, soluble granules 54 of phosphoroamidothioates, preferably acephate.

The dust free soluble granules 54 were tested for required quality specifications and packed in desired packing. This technique gives 99% of conversion yield. The dust free soluble granules 54 enjoy all the formulation advantages described above, producing dust free soluble granules 54 which are beneficial from an economic aspect and a handling aspect and which show a very good performance during use.

The following examples are presented to illustrate but not to restrict the present invention. Parts and percentage are by weight unless otherwise specified.

EXAMPLE 1

Acephate 97% Granules can be prepared as follows:

Composition

| Ingredients | Quantity (% w/w) |
|---|---|
| Acephate Technical 98.5% purity | 98.48 |
| Dispersing agent | 0.50 |
| Wetting agent | 0.10 |
| Binding agent | 0.10 |
| Antifoaming agent | 0.03 |
| Disintegrating agent | 0.50 |
| Stabilizer | 0.05 |
| Filler | 0.24 |
| Total | 100.00 |

EXAMPLE 1 PROCESS

The constituents of the above composition are mixed in a pre-mixer, then ground in a microniser to the required size of 5 micron to 10 micron. The ground product 24 is again mixed in a post-mixer to get a uniform homogeneous mixture 28. This homogeneous mixture 28 is then fed through a rotary feeder into a low compaction granulator, while maintaining an inlet temperature of 32 to 35° C. and an outlet temperature of 40 to 45° C. The Acephate granules 36 formed in the granulator are further dried through an air chamber, sized to 1.5 mm to 3 mm length, and are collected. The fines 50 generated during the process are recharged to get a conversion yield of 99 percent.

EXAMPLE 2

Acephate 98% granules can be prepared as follows:

Composition

| Ingredient | Quantity (% w/w) |
|---|---|
| Acephate Technical 98.5% purity | 99.50 |
| Dispersing agent | 0.25 |
| Wetting agent | 0.03 |
| Binding agent | 0.05 |
| Antifoaming agent | 0.02 |
| Disintegrating agent | 0.05 |
| Stabilizer | 0.05 |
| Filler | 0.05 |
| Total | 100.00 |

Acephate 98% granules with above composition can be prepared by following the process described in EXAMPLE 1.

EXAMPLE 3

Acephate 97.5% granules can be prepared as follows:
Composition

| Ingredient | Quantity (% w/w) |
| --- | --- |
| Acephate Technical 98.5% purity | 98.99 |
| Dispersing agent | 0.40 |
| Wetting agent | 0.10 |
| Binding agent | 0.10 |
| Antifoaming agent | 0.03 |
| Disintegrating agent | 0.20 |
| Stabilizer | 0.05 |
| Filler | 0.13 |
| Total | 100.00 |

Acephate 97.5% granules with above composition can be prepared by following the process described in EXAMPLE 1.

EXAMPLE 4

Acephate 90% Granules can be prepared as follows:
Composition

| Ingredient | Quantity (% w/w) |
| --- | --- |
| Acephate Technical 98.5% purity | 91.38 |
| Dispersing agent | 00.75 |
| Wetting agent | 00.10 |
| Binding agent | 00.20 |
| Antifoaming agent | 00.03 |
| Disintegrating agent | 01.00 |
| Stabilizer | 00.50 |
| Filler | 06.04 |
| Total | 100.00 |

Acephate 90% granules with above composition can be prepared by following the process described in EXAMPLE 1.

EXAMPLE 5

Acephate 85% granules can be prepared as follows:
Composition

| Ingredient | Quantity (% w/w) |
| --- | --- |
| Acephate Technical 98.5% purity | 86.30 |
| Dispersing agent | 01.50 |
| Wetting agent | 00.50 |
| Binding agent | 01.00 |
| Antifoamer | 00.05 |
| Disintegrating agent | 02.00 |
| Stabilizer | 00.60 |
| Filler | 08.05 |
| Total | 100.00 |

Acephate 85% granules with above composition can be prepared by following the process described in EXAMPLE 1.

EXAMPLE 6

Acephate 75% Granules can be prepared as follows:
Composition

| Ingredient | Quantity (% w/w) |
| --- | --- |
| Acephate Technical 98.5% purity | 76.15 |
| Dispersing agent | 2.00 |
| Wetting agent | 1.50 |
| Binding agent | 1.50 |
| Antifoaming agent | 0.06 |
| Disintegrating agent | 5.00 |
| Stabilizer | 0.75 |
| Filler | 13.04 |
| Total | 100.00 |

Acephate 75% Granules with above composition can be prepared by following the process described in EXAMPLE 1.

EXAMPLE 7

Acephate 50% Granules can be prepared as follows:
Composition

| Ingredients | Quantity (% w/w) |
| --- | --- |
| Acephate Technical 98.5% purity | 50.77 |
| Dispersing agent | 3.00 |
| Wetting agent | 2.00 |
| Binding agent | 3.00 |
| Antifoaming agent | 0.08 |
| Disintegrating agent | 10.00 |
| Stabilizer | 1.00 |
| Filler | 30.15 |
| Total | 100.00 |

Acephate 50% Granules with above composition can be prepared by following the process described in EXAMPLE 1.

EXAMPLE 8

Acephate 40% granules can be prepared as follows:
Composition

| Ingredient | Quantity (% w/w) |
| --- | --- |
| Acephate Technical 98.5% purity | 40.61 |
| Dispersing agent | 4.50 |
| Wetting agent | 3.00 |
| Binding agent | 3.00 |
| Antifoaming agent | 0.08 |
| Disintegrating agent | 12.00 |
| Stabilizer | 1.50 |
| Filler | 35.31 |
| Total | 100.00 |

Acephate 40% Granules of above composition can be prepared by following the process described in EXAMPLE 1.

Tests

The physical properties of Acephate granules were determined before and after aging at 45° C. for 500 hrs and for flowability, wetting time, attrition test, disintegration rate, tap density, suspensibility, sedimentation and persistent foam. No noticeable difference in all the above properties was observed. The dynamic wetting time and solubility test was measured as per MT-167 of CIPAC. The flowability was measured as per MT-172 of CIPAC. The dry sieve analysis was measured as per MT-170 of CIPAC. The sedimentation was measured as per MT-15.1 of CIPAC. Dustiness of granules was measured as per MT-171 of CIPAC. The tap density was measured as per MT-58.4 and MT-33 of CIPAC. The Acephate technical was determined by the GLC method published in AOAC.

Although the present invention has been disclosed in terms of a preferred embodiment, it will be understood that numerous additional modifications and variations can be made without departing from the scope of the invention as defined by the following claims.

What is claimed is:

1. A process for preparing soluble granules comprising
   a) premixing 40 to 98 wt. % an insecticidally active compound of the following formula:

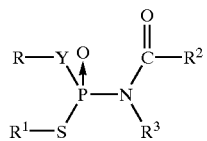

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur;
   0.1–5.0 wt. % a dispersing agent; 0.1–3.0 wt. % a wetting agent; 0.1–3.0 wt. % a binding agent; 0.01–0.08 wt. % an antifoaming agent; 0.01–10.0 wt. % a disintegrating agent; 0.01–1.0 wt. % a stabilizer; and fillers to make 100 wt. %, to form a premix comprising essentially 95–99% solids and 1–5% moisture and/or solids;
   b) grinding said premix to produce a ground product having a predetermined particle size;
   c) post-mixing said ground product to produce a mixture;
   d) granulating said mixture to produce granules;
   e) drying said granules to produce dry granules;
   f) sizing said dry granules to produce sized granules having a predetermined length and a predetermined diameter; and
   g) sieving said sized granules to separate fines which are less than said predetermined length and said predetermined diameter.

2. The process of claim 1, wherein said ground product has a predetermined particle size of 5–10 microns.

3. The process of claim 1, wherein said dry granules have a predetermined length of 1.5–3.0 mm.

4. The process of claim 1, wherein said dry granules have a predetermined diameter of 0.5 to 1.0 mm.

5. The process claimed in claim 1, wherein said fillers are solids in powder form.

6. The process of claim 1, wherein said binding agent is a blend of sucrose and starch derivatives.

7. The process of claim 1, wherein said wetting agent is selected from the group comprising calcium salt of alkyl aryl sulphonate and sodium salt of alkyl aryl sulphonate.

8. The process of claim 1, wherein said dispersing agent is a derivative of sulfonated fatty alcohol.

9. The process of claim 1, wherein said disintegrating agent is a swelling type clay selected from the group comprising bentonite and zeolite.

10. The process of claim 1, wherein said antifoaming agent is silicon oil derivative.

11. The process of claim 1, wherein said stabilizer is a salt of a higher fatty acid.

12. The process of claim 1, wherein said fillers are selected from the group comprising precipitated silica and kaoline.

13. The process of claim 1, wherein said granulation is accomplished by passing said mixture through an orifice having and inlet and an outlet.

14. The process of claim 13, wherein said inlet has a temperature of 30–35° C.

15. The process of claim 13, wherein said outlet has a temperature of 40–45° C.

16. The process of claim 1, wherein said drying is accomplished by passing said granules though an air chamber.

17. The process of claim 1, wherein said grinding is accomplished by a microniser.

18. The process of claim 1, wherein said sizing is accomplished by an oscillating cutter.

19. The process of claim 1, wherein said insecticidally active compound is acephate.

20. The process of claim 1, further comprising;
   h) recycling said fines into step d).

21. The process of claim 20, wherein said insecticidally active compound is acephate.

22. The process of claim 21, wherein said ground product has a predetermined particle size of 5–10 microns.

23. The process of claim 22, wherein said dry granules have a predetermined length of 1.5–3.0 mm and a predetermined diameter of 0.5 to 1.0 mm.

24. The process of claim 23, wherein said binding agent is a blend of sucrose and starch derivatives.

25. The process of claim 24, wherein said wetting agent is selected from the group comprising calcium salt of alkyl aryl sulphonate and sodium salt of alkyl aryl sulphonate.

26. The process of claim 25, wherein said dispersing agent is a derivative of sulfonated fatty alcohol.

27. The process of claim 26, wherein said disintegrating agent is a swelling type clay selected from the group comprising bentonite and zeolite.

28. The process of claim 27, wherein said antifoaming agent is silicon oil derivative.

29. The process of claim 28, wherein said stabilizer is a salt of a higher fatty acid.

30. The process of claim 29, wherein said fillers are selected from the group comprising precipitated silica and kaoline.

31. The process of claim 20, wherein said granulation is accomplished by passing said mixture through an orifice having and inlet and an outlet.

32. The process of claim 31, wherein said inlet has a temperature of 30–35° C. and said outlet has a temperature of 40–45° C.

33. The process of claim 32, wherein said drying is accomplished by passing said granules though an air chamber.

34. The process of claim 33, wherein said grinding is accomplished by a microniser.

35. The process of claim 34, wherein said sizing is accomplished by an oscillating cutter.

36. A process for preparing soluble granules comprising
   a) preparing a dry premix by premixing 40 to 98 wt. % an insecticidally active compound of the following formula:

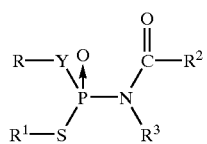

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur;

0.1–3.0 wt. % a wetting agent and a filler to make 100 wt. %;

b) grinding said dry premix to produce a ground product having a predetermined particle size;

c) post-mixing said ground product to produce a mixture;

d) granulating said mixture to produce granules;

e) drying said granules to produce dry granules;

f) sizing said dry granules to produce granules having a predetermined length and a predetermined diameter; and g) sieving said sized granules to separate fines which are less than said predetermined length and said predetermined diameter.

37. The process of claim 36, wherein said wetting agent is selected from the group comprising calcium salt of alkyl aryl sulphonate and sodium salt of alkyl aryl sulphonate.

38. The process of claim 36, wherein said filler is selected from the group comprising precipitated silica and kaoline.

39. The process of claim 38, wherein said wetting agent is selected from the group comprising calcium salt of alkyl aryl sulphonate and sodium salt of alkyl aryl sulphonate.

40. The process of claim 36, wherein said step of preparing said dry premix further comprises premixing 0.1–5.0 wt. % a dispersing agent.

41. The process of claim 40, wherein said dispersing agent is a derivative of sulfonated fatty alcohol.

42. The process of claim 36, wherein said step of preparing said dry premix further comprises premixing 0.1–3.0 wt. % a binding agent.

43. The process of claim 42, wherein said binding agent is a blend of sucrose and starch derivatives.

44. The process of claim 36, wherein said step of preparing said dry premix further comprises premixing 0.01–0.08 wt. % an antifoaming agent.

45. The process of claim 44, wherein said antifoaming agent is a silicon oil derivative.

46. The process of claim 36, wherein said step of preparing said dry premix further comprises premixing 0.01–10 wt. % a disintegrating agent.

47. The process of claim 46, wherein said disintegrating agent is a swelling type clay selected from the group comprising bentonite and zeolite.

48. The process of claim 36, wherein said step of preparing said dry premix further comprises premixing 0.01–1.0 wt. % a stabilizer.

49. The process of claim 48, wherein said stabilizer is a salt of a higher fatty acid.

50. The process of claim 36, wherein said insecticidally active compound is acephate.

51. The process of claim 36, further comprising:
h) recycling said fines into step d).

52. The process of claim 51, wherein said insecticidally active compound is acephate.

53. The process of claim 36, wherein said dry premix is substantially free from water or solvent.

54. The process of claim 36, wherein said step of preparing said dry premix further comprises premixing 0.1–5.0 wt. % a dispersing agent, 0.1–3.0 wt. % a binding agent, 0.01–0.08 wt. % an antifoaming agent, 0.01–10 wt. % a disintegrating agent, 0.01–1.0 wt. % a stabilizer.

55. The process of claim 54, wherein said insecticidally active compound is acephate.

56. The process of claim 55, wherein said dispersing agent is a derivative of sulfonated fatty alcohol, said binding agent is a blend of socrose and starch derivatives, said antifoaming agent is a silicon oil derivative, said disintegrating agent is selected from the group comprising bentonite and zeolite, and said stabilizer is a salt of a higher fatty acid.

57. The process of claim 56, wherein said dry premix is substantially free of water or solvent.

58. The process of claim 54, wherein said dry premix is substantially free of water or solvent.

59. A process for preparing soluble granules consisting essentially, a) preparing a dry premix by premixing 40 to 98 wt. % an insecticidally active compound of the following formula:

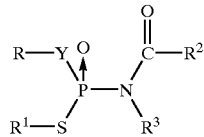

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur;

0.1–5.0 wt. % a dispersing agent; 0.1–3.0 wt. % a wetting agent; 0.1–3.0 wt. % a binding agent; 0.01–0.08 wt. % an antifoaming agent; 0.01–10.0 wt. % a disintegrating agent; 0.01–1.0 wt. % a stabilizer; and a filler to make 100 wt. %;

b) grinding said dry premix to produce a ground product having a predetermined particle size;

c) post-mixing said ground product to produce a mixture;

d) granulating said mixture to produce granules;

e) drying said granules to produce dry granules;

f) sizing said dry granules to produce granules having a predetermined length and a predetermined diameter; and g) sieving said sized granules to separate fines which are less than said predetermined length and said predetermined diameter.

60. The process of claim 59, wherein said binding agent is a blend of sucrose and starch derivatives.

61. The process of claim 59, wherein said wetting agent is selected from the group comprising calcium salt of alkyl aryl sulphonate and sodium salt of alkyl aryl sulphonate.

62. The process of claim 59, wherein said dispersing agent is a derivative of sulfonated fatty alcohol.

63. The process of claim 59, wherein said disintegrating agent is a swelling type clay selected from the group comprising bentonite and zeolite.

64. The process of claim 59, wherein said antifoaming agent is silicon oil derivative.

65. The process of claim 59, wherein said stabilizer is a salt of a higher fatty acid.

66. The process of claim 59, wherein said filler is selected from the group comprising precipitated silica and kaoline.

67. The process of claim 59, wherein said insecticidally active compound is acephate.

68. The process of claim 59, wherein said dry premix is substantially free of water or solvent.

* * * * *